United States Patent
Boersma et al.

(10) Patent No.: US 12,385,891 B2
(45) Date of Patent: Aug. 12, 2025

(54) CAPACITIVE HYDROGEN SENSOR

(71) Applicant: Nederlandse Organisatie voor toegepast-natuurwetenschappelijk onderzoek TNO, 's-Gravenhage (NL)

(72) Inventors: Arjen Boersma, Haaren (NL); Jörgen Sweelssen, Mierlo (NL); Huibert Blokland, Noordeloos (NL); Renz Jeroen Van Ee, Houten (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 350 days.

(21) Appl. No.: 17/434,406

(22) PCT Filed: Feb. 27, 2020

(86) PCT No.: PCT/NL2020/050127
§ 371 (c)(1),
(2) Date: Aug. 26, 2021

(87) PCT Pub. No.: WO2020/175994
PCT Pub. Date: Sep. 3, 2020

(65) Prior Publication Data
US 2022/0042958 A1     Feb. 10, 2022

(30) Foreign Application Priority Data
Feb. 27, 2019   (EP) .................................. 19159764

(51) Int. Cl.
*G01N 33/00* (2006.01)
*G01N 27/22* (2006.01)

(52) U.S. Cl.
CPC ......... *G01N 33/005* (2013.01); *G01N 27/227* (2013.01)

(58) Field of Classification Search
CPC .......................... G01N 33/005; G01N 27/227
(Continued)

(56) References Cited

U.S. PATENT DOCUMENTS

| | | | |
|---|---|---|---|
| 9,618,465 B2 | 4/2017 | Kocanda et al. | |
| 10,001,448 B2 * | 6/2018 | Luebke | G01N 27/02 |

(Continued)

FOREIGN PATENT DOCUMENTS

| | | |
|---|---|---|
| EP | 2 623 968 A1 | 8/2013 |
| JP | 2013228346 A * | 11/2013 |
| WO | 2015/158272 A1 | 10/2015 |

OTHER PUBLICATIONS

Lallan Yadava et al. "A Titanium Dioxide-Based MOS Hydrogen Sensor" Solid-State Electronics, 1990, op. 1229-1234, vol. 33 No. 10.

(Continued)

*Primary Examiner* — Peter J Macchiarolo
*Assistant Examiner* — Rodney T Frank
(74) *Attorney, Agent, or Firm* — Studebaker Brackett PLLC

(57) ABSTRACT

The invention relates to a capacitive sensing material and a method of manufacturing thereof, a capacitive sensing coating formulation, a capacitive chip, a capacitive sensor, a method for manufacturing a coated chip, a method for analysing the composition of a gaseous mixture, a use of particles comprising titanium oxide and platinum for sensing hydrogen, and a use of capacitive sensing material for detecting a gas leak. The capacitive sensing material comprises composite particles wherein porous titanium dioxide is at least in part coated with platinum particles.

22 Claims, 4 Drawing Sheets

(58) Field of Classification Search
USPC .......................................................... 73/23.2
See application file for complete search history.

(56) References Cited

U.S. PATENT DOCUMENTS

2008/0175345 A1    7/2008  Hill et al.
2014/0326615 A1   11/2014  Kocanda et al.
2017/0059538 A1    3/2017  Noh et al.

OTHER PUBLICATIONS

Buse Comert et al. "Titanium Dioxide Thin Films as Methane Gas Sensors" IEEE Sensors Journal, Dec. 15, 2016, pp. 8890-8896, vol. 16 No. 24.
International Search Report issued in PCT/NL2020/050127; mailed Apr. 14, 2020.
Weerasak Chomkitichai et al. "Flame-Made Pt-Loaded TiO2 Thin Films and Their Application as H2 Gas Sensors" Journal of Nanomaterials, 2013, pp. 1-8, vol. 2013.
Tarek A. Kandiel et al. "Mesoporous TiO2 Nanostructures: A Route to Minimize Pt Loading on Titania Photocatalysts for Hydrogen Production" Physical Chemistry Chemical Physics, Oct. 12, 2011, pp. 20155-20161, vol. 13, No. 45.

\* cited by examiner

CAPACITIVE HYDROGEN SENSOR

The invention relates to a capacitive sensing material and a method of manufacturing thereof, a capacitive sensing coating formulation, a capacitive chip, a capacitive sensor, a method for manufacturing a coated chip, a method for analysing the composition of a gaseous mixture, a use of particles comprising titanium oxide and platinum for sensing hydrogen, and a use of capacitive sensing material for detecting a gas leak.

Sensors are important devices in electronic equipment. Primarily proximity sensors, such as capacitive sensors, find their use in different applications ranging from touchscreens to measuring humidity. Capacitive sensors make use of capacitive coupling, i.e. detecting and measuring a change in capacitance. Several examples of sensors that use capacitive sensing include sensors to detect and measure proximity, position and displacement, force, humidity, fluid level, acceleration, gas saturation and composition etc.

As a byproduct of numerous industrial processes, hydrogen has historically been burned for heat, for lack of other valuable uses. The situation resembles natural gas flaring at oil wells. Several countries, such as Japan focus on developing carbon-free technology to generate hydrogen as a key step in becoming a "hydrogen society". In addition, some countries mix hydrogen with traditional fuel gas (coal and natural gas) in an attempt to reduce the use of fossil fuels, especially those countries which are fully dependent on imported fossil fuels. Global climate objectives contribute as well hereto, resulting in the addition of hydrogen to natural gas.

As a consequence, there is an increasing need for frequent inline measurement of gas composition. At present, chromatography is commonly used for quantitatively and qualitatively determining the composition of gas mixtures. Accordingly, the sensor units based on (gas) chromatography are typically large, complex, and expensive, since they comprise at least a sampling unit, a gas separation column, and a detector. Moreover, they need storage containers for carrier gas and calibration gas.

A need exists for relatively inexpensive and more practical sensors and methods for determining the composition of gas mixtures with high accuracy.

For example, US-A-2017/0 059 538 describes a hydrogen sensor comprising chemochromic nanoparticles having improved properties in determining hydrogen. The chemochromic material reacts with hydrogen, resulting in a change in colour, transmission/reflection properties or other optical properties. The resulting change in colour, transmission/reflection or other optical properties is evaluated either by the naked eye, a spectrophotometer, or a photodetector.

U.S. Pat. No. 9,618,465 relates to a palladium-based hydrogen sensor which relies upon measuring electrical impedance (i.e. resistance). Temperature and the presence of oxygen are key parameters to the measurable hydrogen concentration. In addition, the sensitivity of the sensor depends on the distribution of the palladium isles on the dielectric substrate between the electrodes.

EP-A-2 623 968 relates to a gas sensor comprising a gate electrode in which platinum crystal grains are surrounded with a metal oxide mixture obtained by mixing oxygen-doped amorphous metal with crystalline metal oxide.

WO-A-2015/158272 describes to a method for manufacturing a hydrogen gas sensor by using noble metal doped titanium dioxide nanopowder. The method encompasses a sintering step at a temperature of 350-600° C. The resulting sensor is a sintered nanoblock having electrodes on its surface.

US-A-2008/0 175 345 relates to a sampling system for taking samples from the atmosphere in a reactor containment of a nuclear plant. The system can comprise a gas analyser, in particular a capacitive polymer sensor for analysing hydrogen.

Yadava et al. (*Solid-State Electronics* 1990, 33(10), 1229-1234) describe a titanium dioxide-based metal oxide semiconductor sensor suitable for detecting low concentrations of hydrogen in gas streams. The sensor comprises palladium isles as top electrodes for adsorbing hydrogen gas.

Comert et al. (*IEEE Sens. J.* 2016, 16(24), 8890-8896) reveal a methane gas sensor comprising interdigitated platinum electrodes onto which a thin film of titanium dioxide particles having an average particle size of 10 nm is deposited. The sensor measurements are based on a change in resistance.

Kandiel et al. (Phys. Chem. Chem. Phys. 2011, 13, 20155-20161) describe a titanium-based photocatalyst having a very small amount (0.1-1.0 wt. %) of platinum loading for hydrogen evolution from methanol. The particle size of 3.5-8 nm, which is typically suitable for catalysis, rules out its effectiveness as sensing material.

Chomkitichai et al. (*J. Nanomater.* 2013, 2013, 1-8) describe hydrogen gas sensors using small-sized, flame-made, platinum-loaded titanium dioxide nanoparticles that measure resistance at temperatures above 300° C. for adequate sensing response.

An objective of the invention is to provide capacitive sensing material which addresses, at least part of, one or more disadvantages faced in the art.

Also an objective of the invention is to provide a cost efficient and simple to use sensor with which the composition of a gaseous mixture can be relatively easy determined.

The inventors surprisingly found that one or more of these objectives can, at least in part, be met by using a material, for example as part of a sensor, which can take up high amounts of gases, preferably such as hydrogen. The capacitive sensing material contributes advantageously to for example the ease of detecting gases at varying conditions, robustness of the sensor, cost efficiency, and ease of deployment in the field.

Accordingly, in a first aspect the invention relates to a capacitive sensing material, comprising composite particles wherein porous titanium dioxide is at least in part coated with platinum particles.

According to another aspect of the invention, there is provided a capacitive sensing coating formulation, comprising a capacitive sensing material as described herein.

According to another aspect of the invention, there is provided a capacitive chip, comprising the capacitive sensing material as described herein or a capacitive sensing coating formulation as described herein.

According to another aspect of the invention, there is provided a capacitive sensor, comprising the capacitive sensing material as described herein and/or the capacitive chip as described herein.

According to another aspect, the invention relates to a method for manufacturing the capacitive sensing material as described herein, the method comprising:
  i) preparing a dispersion comprising porous titanium dioxide particles, and
  ii) coating the porous titanium dioxide particles with platinum particles, thereby forming the capacitive sensing material.

According to another aspect, the invention relates to a method for manufacturing a coated chip, preferably a capacitive chip as described herein, comprising:
i) applying a capacitive sensing material as described herein and/or a capacitive sensing coating formulation as described herein onto a chip, thereby forming a coated chip.

According to another aspect, the invention relates to a method for sensing a gas in a gaseous mixture, wherein the gaseous mixture preferably comprises at least hydrogen, the method comprising:
i) contacting the gaseous mixture with the capacitive sensing material as described herein, and
ii) measuring a change in dielectric properties of the capacitive sensing material.

According to another aspect, the invention relates to a use of particles comprising titanium oxide and platinum for sensing hydrogen.

The invention also relates to a use of capacitive sensing material as described herein for detecting a gas leak.

Figure 1:
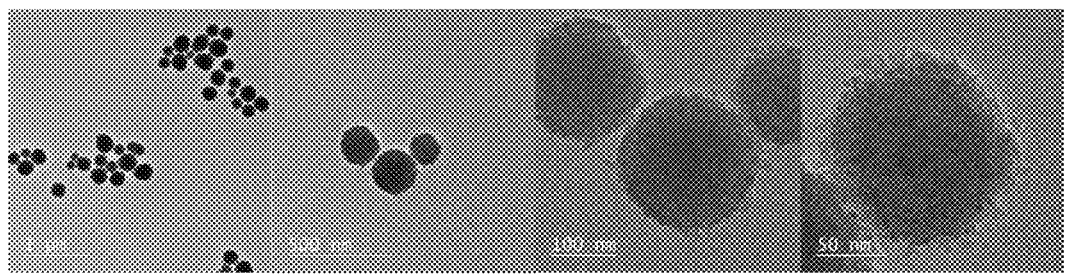
FIG. 1 shows that the porous titanium dioxide particles have an average particle size of 300 nm.

The term "chip" as described herein is meant to comprise a piece of material, such as semiconductor material, onto which an electrode layout is manufactured. The chip may be part of a "wafer". The term "chip" includes in the context of the invention microchip and nanochip.

The term "coating" as used herein is meant to include both the single and plural of a layer on the surface of, e.g. a chip, such as the capacitive chip as described herein, layer on the surface of a substrate, such as an insulating or semiconductive material, layer on the surface of a particle or substance, such as porous titanium dioxide, and a layer on the inner surface of a particle or substance, e.g. within pores, and may include, for example a layer of discrete particles, a layer of a continuous material, and a layer comprising discrete particles in a layer of a continuous matrix material. In particular, the sensing material as described comprises composite particles wherein a layer of discrete platinum particles is present on the porous titanium dioxide. The porous titanium dioxide may be completely or incompletely covered with platinum particles. The term "coating" includes both complete and incomplete coverage of the surface of a substrate with, e.g. a material, substance or particles.

The term "fuel gas" is used to denote a gaseous mixture. The term includes for example natural gas, coal gas, biogas and combinations thereof. Although such gas streams are mostly used as fuel, they are defined herein by their composition and are not restricted to a particular use.

The term "inline" refers to an analyser which is connected to a process or stream and conducts automatic sampling or does not need sampling and is based on continuous flow (either of the main stream or of a side stream).

The term "sensing material" in "capacitive sensing material" as used herein includes terms, such as "coating", "smart material", "responsive material", and "stimuli-responsive material". The term may broadly refer to: layer on the surface of, e.g. a chip, such as a capacitive chip as described herein, layer on the surface of a substrate, such as an insulating or semiconductive material, and may include, for example a layer of discrete particles, a layer of a continuous material, and a layer comprising discrete particles in a layer of a continuous matrix material. In particular, the sensing material as described herein includes a layer of discrete particles. The sensing material may completely or incompletely cover a surface. Thus, the capacitive sensing material as described herein may be in the form of a coating.

The term "sensor element" as described herein is meant to include the sensing material, in particular a substrate, e.g. a chip, coated with the capacitive sensing material, and the capacitive chip as described herein. The term "sensor" refers to a single sensor element or a plurality of sensor elements in combination with a casing or housing, and typically comprises components, such as electronics, e.g. a transducer and/or capacitator, a processor, and/or a memory device. In case of a plurality of sensor elements, the elements may be spatially separated and arranged such that each sensor element has a surface for exposure to for example an atmosphere. In addition, the term is meant to include the capacitive sensor as described herein. The casing preferably comprises a chamber to which the sensor elements are exposed and wherein the chamber is provided with at least one opening for a gas stream.

The invention provides a capacitive sensing material comprising composite particles wherein porous titanium dioxide is at least in part coated with platinum particles. The capacitive sensing material as described herein comprises composite particles of porous titanium dioxide that may preferably comprise smaller platinum particles, and/or contain (even) smaller platinum particles at least in part of the pores of the titanium dioxide. The composite particles, in particular being composite nanoparticles, have an average particle size of 50-500 nm, such as 100-500 nm. The platinum particles, which are preferably nanoparticles, may be impregnated in at least part of the pores of the porous titanium dioxide and may have an average particle size of 1-10 nm. The titanium dioxide is at least in part coated (covered) with platinum, or platinum particles, e.g. a layer of platinum particles. The efficiency of the sensing properties of the capacitive sensing material depends on the size and/or amount of the platinum particles. When these platinum particles are too small (i.e., typical particle size for catalyst particles, such as below about 1 nm), they do not have sufficient metallic properties, whereas when these are too large (i.e. above about 20 nm), they may form a connected conductive path, which is unsuitable for capacitive measurements. With too large platinum particles, the sorption of gas molecules by the capacitive sensing material may result in damage, or even cracks, and therefore reduce the lifespan of the material.

For the capacitive sensing material, the relative permittivity or capacitance of the material changes as a function of the partial pressure of the gaseous absorbent. The change in capacitance is influenced typically by the change in dielectric constant and by the swelling of the material caused by absorption of the gaseous component. Based on the effect of the thickness on the change in capacitance due to absorption of gas, it was found that the highest sensitivity is obtained with the preferred average particle size of the platinum particles of 1-20 nm, and more preferably 2-10 nm, preferably in combination with a sensor active area of 0.5-2 mm$^2$ for each sensor element, and a thickness of the layer of the sensing material on the sensor element of 1-10 μm. The average particle size of the composite particles, porous titanium dioxide particles, and the platinum particles can be measured with techniques known in the art, such as transmission electron microscopy (TEM).

Sensing materials may detect the presence of various types of gases by measuring the change in capacitance, or change in dielectric constant of the material due to absorption and/or adsorption of at least one of the various types of gases. In general, atmospheric oxygen residing on (the) sensing material, such as the metal oxide surface, is reduced by the target gases, allowing more electrons in the conduction band of the metal oxide. This resistance drop is reversible and varies depending on the composition of the capacitive sensing material, and working conditions, such as temperature, humidity and atmospheric pressure. The inventors surprisingly found that the capacitive sensing material of the invention does not require the presence of oxygen to be applicable in measuring gases, such as hydrogen. Hence, in an embodiment the capacitive sensing material as described herein can be used for measuring gases in an oxygen-free environment. The capacitive sensing material as described herein can surprisingly be used at room temperature.

The porous titanium dioxide suitably holds particles, such as platinum (nano)particles, in its pores. Hence, the pores of the porous titanium dioxide may be at least in part filled with platinum (nano)particles. The (average) porosity of the titanium dioxide, as measured by mercury porosimetry, may be 80% or less, and 10% or more, such as 25% or more, or 40% or more, such as 50-80%, or 60-75%. It was surprisingly found that platinum may at least in part be present in the pores of titanium dioxide, whereas palladium tend to grow primarily on the outside of the titanium dioxide. In addition, the capacitive sensing material according to the invention has surprisingly high efficiency. This is believed to be caused by the high surface adsorption of hydrogen to the platinum particles. Consequently, the higher the surface area of the platinum particles the higher the hydrogen adsorption.

The capacitive sensing material as described herein may further comprise a dopant. In particular, the dopant may be inserted into the bulk of the capacitive sensing material, i.e. in the composite particles, in a certain concentration to (positively) alter the electric property of the material. The dopant may be inserted into the porous titanium dioxide and/or the platinum particles, preferably into the platinum particles. In case a dopant is added, the surface of the platinum particles present in the capacitive sensing material preferably has to be available to adsorption and/or absorption of gases, e.g. hydrogen. The dopant may comprise one or more electron acceptors selected from the group consisting of, for example boron, aluminium, gallium, beryllium, zinc, silver, cadmium, silicon, or germanium, one or more electron donors selected from the group consisting of, for example phosphorus, arsenic, antimony, selenium, tellurium, silicon, or germanium, or a mixture of electron acceptor(s) and electron donor(s). The concentration of the dopant may be 0-5% by total weight of the sensing material, such as 0.05-2.5%, 0.1-1.8%, or 0.1-1%.

In particular, the porous titanium dioxide may be amorphous, since after the synthesis thereof no hydrothermal treatment is required to be applied to increase the crystallinity. The porous titanium dioxide may be characterised by a crystallinity percentage, i.e. an amount of crystalline (porous) titanium dioxide, as measured by Raman spectroscopy or X-ray diffraction, of 0-35% by total amount of porous titanium dioxide, such as 0.5-20%, 1-15%, or 1-10%.

As is known in the art, humidity may negatively influence the sensing capabilities of capacitive sensing material, e.g. affecting the capacitance. Since a particular application of the capacitive sensing material as described herein will be in sensors, e.g. used in fuel gases—from which most of the water has been extracted, the influence of water may only be small. In addition, a sensor (array) comprising the capacitive sensing material as described herein may further comprise an additional (capacitive) sensor element that can measure the water concentration in the gas mixture, and/or enable correction.

The capacitive sensing material may comprise 10-80% of titanium dioxide, based on the total weight of the composite particles. In particular, the amount of titanium dioxide may be 10% or more and 60% or less by total weight of the composite particles, such as 10-50%, 10-45%, or 15-45%. Preferably, the amount of titanium dioxide in the capacitive sensing material is 20-45% by total weight of the composite particles, more preferably 30-40%.

The capacitive sensing material may comprise 5-60% by total weight of the composite particles of platinum. In particular, the amount of platinum may be 5-50% by total weight of the composite particles, such as 5-45%, 10-45%, 12-45%, or 15-45%. Preferably, the amount of platinum in the capacitive sensing material is 10-45%, such as 20-45% by total weight of the composite particles.

The mass ratio of titanium dioxide and platinum in the capacitive sensing material may be 1:5 to 5:1. In particular, the mass ratio may be 1:3 to 3:1. Preferably, the mass ratio is about 1:1.

In an embodiment, the capacitive sensing material comprises composite particles wherein 20-50 wt. % is porous titanium dioxide and 10-50 wt. %, such as 20-50 wt. %, is platinum particles by total weight of the capacitive sensing material.

The shape of the particles of the capacitive sensing material as described herein may depend on the application of the capacitive sensing material. There are many descriptive terms that can be applied to the particle's shape. Several shape classifications include, cubic, cylindrical, such as barrels, rods and pillars, discoidal, ellipsoidal, equant, irregular, polygon, polyhedron, round, spherical, square, tabular, and triangular. In particular, the shape of the particles may be classified as round. Preferably, the shape of the particles is spherical, rounded polyhedron, rounded polygon, such as poker chip, corn, pill, rounded cylinder, such as capsule, faceted. More preferably, the particles as described herein are spherical, cylindrical, or ellipsoidal.

In particular, the composite particles of the capacitive sensing material may be composite nanoparticles because of their increased surface area to volume ratio when compared to microparticles. The inventors found that the presence of platinum as (nano)particles in the pores of the porous titanium dioxide contributes to prevent bursting of the capacitive sensing material upon absorption of gas molecules, such as hydrogen, therefore overcoming a key common-faced issue with gas sensors known in the art. Consequently, high concentrations of gases can be measured with the capacitive sensing material as described herein. The invention allows gases, in particular hydrogen, to be measured, for example, in a range of 125-1 000 000 ppm.

The composite particles of the capacitive sensing material as described herein have an average particle size, as measured by transmission electron microscopy, of 40 nm or more, such as 50 nm or more, 60 or more, or 80 nm or more, and 500 nm or less, such as 450 nm or less, 400 nm or less, 350 nm or less, or 300 or less. In particular, the average particle size of the composite particles is 50 nm or more, such as 70 nm or more, or 90 nm or more, and 300 nm or less, such as 275 nm or less, or 200 nm or less. Preferably, the average particle size is 100-300 nm, such as 100-250 nm, or 100-200 nm. In addition, the average particle size of the platinum particles, as measured with transmission electron microscopy, may be 1 nm or more, such as 2 nm or more, 3 nm or more, or 5 nm or more, and 50 nm or less, such as 40 nm or less, or 35 nm or less. In particular, the average particle size of the platinum particles is 1 nm or more, and 30 nm or less, such as 1-20 nm, or 1-15 nm. Preferably, the average particle size of the platinum particles is 2-10 nm.

The capacitive sensing material as described herein may be sensitive to liquids, such as water and/or to gases, such as carbon dioxide, methane, ethane, propane, and hydrogen. The capacitive sensing material of the invention is sensitive to gases, preferably at least to hydrogen. More preferably, the capacitive sensing material according to the invention is sensitive to hydrogen. That is, the capacitive sensing material has a property that is responsive to one or more liquids and/or to one or more gases when exposed thereto. Exposure of the capacitive sensing material to gases causes the gases to be adsorbed and/or absorbed, preferably adsorbed. In particular, the inventors found that the capacitive sensing material of the invention has extraordinary adsorption sensitivity to hydrogen (gas). Preferred responsive properties of the capacitive sensing material include the dielectric constant, conductivity, refractive index, density, volume, and mass. More preferably, the responsive property of the capacitive sensing material is the dielectric constant. Sorption of gas to the capacitive sensing material can cause a change of one or more of these properties of the capacitive sensing material. In particular, the capacitive sensing material of the invention has the property of dielectric constant which is responsive. The property is typically measured for the capacitive sensing material, including sorbed components.

The capacitive sensing material as described herein may additionally comprise components, for example reducing agents, shape controlling agents, dispersants and/or surfactants, such as poly(vinyl pyrrolidone). The additional component(s) may or may not have a responsive property. In case the capacitive sensing material comprises such (a) component(s), the component is preferably part of a part of the composite particles. In addition, the capacitive sensing material may comprise components that do not have a responsive property, which components may or may not comprise metal oxide and/or metal.

The invention also provides a capacitive sensing coating formulation, comprising a capacitive sensing material as described herein. The coating can be applied to surfaces, such as chips, for example, to obtain a capacitive chip as described herein. The coating may comprise a liquid which comprises a capacitive sensing material as described herein. The liquid may be any liquid, such as solvent, suitable for applying the capacitive sensing material onto a surface. In particular, the liquid is water, such as demineralised water. The skilled person understands that the concentration of the capacitive sensing material in the capacitive sensing coating formulation depends on the desired use. For example, when the capacitive sensing coating formulation is used to coat a chip, e.g., to obtain a capacitive chip, the concentration of the capacitive sensing material is selected such that the chip is sufficiently coated for further use. The capacitive sensing coating formulation may advantageously be applied to a surface, such as a chip comprising vulnerable electrodes, without requiring any such high temperature process.

The invention further provides a capacitive chip, comprising the capacitive sensing material as described herein. The capacitive chip may comprise a piece of material, preferably semiconductor material, such as quartz, silicon, gallium arsenide, germanium or any other semiconductor material known in the art, on which electrical conductive tracks are manufactured capable of measuring a capacitance, such as interdigitated electrodes, and on which the capacitive sensing material as described herein is present, as well as electronic circuits, comprising electronic components, such as resistors, transistors, capacitors, inductors and diodes may be present. Alternatively, only the electrodes and the capacitive sensing material are present on the chip, and the chip is connected to the electronic circuits present on a printed circuit board using wire bonds or soldered connections. The electronic circuits may be connected by conductive wires or traces through which electric current can flow, or interconnected by photolithographic techniques on a laminated substrate, such as a printed circuit board. Preferably, in case electronic circuits are present on the capacitive chip, the capacitive sensing material does not completely cover (or coat) the electronic circuits, or does not cover the electronic circuits at all. In particular, the capacitive chip has the property of reading a change in capacitance or dielectric constant of the capacitive sensing material. The capacitive chip as used herein may also include the term "sensor element".

The capacitive chip as described herein may suitably be used in (a) sensor(s), i.e. as a part of a sensor. In an embodiment, the capacitive chip and/or a sensor comprising the capacitive chip is used for measuring gases in an oxygen-free environment, such as hydrogen.

The invention further provides a capacitive sensor, comprising the capacitive sensing material as described herein and/or the capacitive chip as described herein. The capacitive sensor may include a combination of a casing, electronics, a processor, memory device, and one or more sensor elements. The casing preferably comprises a chamber comprising one or more sensor elements, which sensor element(s) is (are) exposed to an atmosphere, preferably the outer atmosphere, because of, for example at least one opening in the chamber and/or casing. The atmosphere is, for example a pure gas comprising a vapour, a gaseous mixture, or a gaseous mixture comprising vapour. The sensor element may be the capacitive chip as described herein, the capacitive sensing material as described herein, which, for example is applied onto a substrate, such as semiconductor material, and applied to a capacitive chip, or a combination of both. In particular, the sensor element comprises the capacitive sensing material as described herein. The capacitive sensing material does not require the presence of oxygen in the atmosphere, hence the atmosphere may comprise a low concentration of oxygen, or be free of oxygen. Hence, in an embodiment, the sensor is used for measuring, e.g. gases, such as hydrogen, in an oxygen-free environment (atmosphere).

The (capacitive) sensor as described herein may comprise more than one sensor elements, such as two, three, four, five, or more sensor elements. A combination of sensor elements can be made, depending on the application and required function of the sensor. For example, the capacitive sensor may be a capacitive gas sensor and/or a capacitive humidity sensor. In case the sensor comprises multiple sensor elements, the sensor may be coined as a multifunctional sensor. Preferably, the multifunctional sensor comprises at least the property of measuring hydrogen.

In an embodiment, a capacitive sensor is provided, comprising the capacitive sensing material as described herein and/or the capacitive chip according to the invention, the sensor being a capacitive gas sensor, preferably having selectivity to detecting hydrogen (gas) and/or determining its concentration.

In another embodiment, a capacitive sensor is provided, comprising two or more capacitive chips, one of which is coated with the capacitive sensing material of the invention, the other capacitive chip(s) coated with other, for example sensing materials responsive to, e.g. methane, ethane, propane, butane, pentane, carbon dioxide, water and nitrogen.

The sensors as described herein may be capable of operating at least in a part of the range of −20° C. to 75° C., more preferably at least in the range of −20° C. to 55° C., and/or preferably at least in a part of the range of 1-100 absolute bar, such as 1-10 absolute bar which is typical for the gas grid. The sensors are described herein do not require heating and/or calcination of the capacitive sensing material. The methods as described herein can, for example, be carried out under these conditions. The sensor is preferably adapted for operating on gas streams having a flow of from about 1l/min (such as in household environments), or up to 1000 $m^3$/h or even 10 000 $m^3$/h (such as in distribution networks). In some embodiments, the (gas) sensor as described herein is resistant to gas streams with up to 5 mg $H_2S$ per $Nm^3$ (i.e. cubic meter at normal conditions), up to 1 mol % aromatic hydrocarbons, up to 5 ppm by volume siloxanes, and/or total sulphur up to 45 mg per $Nm^3$. The person skilled in the art of sensor for natural gas streams is familiar with materials that are resistant to these conditions. The sensor preferably has a power consumption of less than 1 W, more preferably less than 1 mW for battery driven devices. The sensor element preferably has a footprint within 2 cm×2 cm, and preferably fits in a sensor body of 2 cm×2 cm×2 cm. In inline devices any electronics are preferably contained within the casing and sealed-off from a fuel gas stream for better safety.

The invention also provides a method for manufacturing the capacitive sensing material as described herein, the method comprising:
i) preparing a dispersion comprising porous titanium dioxide particles, and
ii) coating the porous titanium dioxide particles with platinum particles, thereby forming the capacitive sensing material.

The method for manufacturing the capacitive sensing material may further comprise one or both of the following optional steps:
removing residual chemicals from the dispersion comprising porous titanium dioxide particles;
centrifuging the sensing material formed in step ii).

Step i) of the method may alternatively be read as preparing or synthesising a dispersion comprising porous titanium dioxide nanoparticles from precursors, such as titanium isopropoxide and potassium chloride. With step i) of the method one or more precursors for the porous titanium dioxide are used, for example titanium isopropoxide, and one or more salts are used, for example potassium chloride. With step ii) the platinum particles may at least in part fill at least part of the pores of the porous titanium dioxide particles. Step ii) of the method is performed using precursors, e.g. chloroplatinic acid and sodium borohydride, at elevated temperatures, to form the capacitive sensing material. Furthermore, with step ii) the capacitive sensing material may be formed by using platinum precursors, such as chloroplatinic acid, and one or more reducing agents, such as sodium borohydride. The preparation of the dispersion and/or the formation of the capacitive sensing material with the method as described herein may be performed at a temperature of 20-150° C. In particular, the temperature is 30° C. or higher and 120° C. or lower, such as 40-100° C., or 50-80° C. Preferably, the temperature is about 60° C. Unlike material known from the art, the capacitive sensing material as described herein does not require calcination or flame pyrolysis.

Metal oxide (semiconductor) materials can be deposited in the form of thick or thin films. An example of such a material is tin dioxide, which is known for targeting volatile organic compounds and carbon monoxide. Thick films (i.e. film thickness of 3-10 μm) are preferred, as they tend to have a suitable porosity, i.e. having an increased surface area. Thick films are typically deposited as a paste and sintered (drop coat or printed). Thin films, on the other hand (sub-micron thickness where surface effect dominates electrical properties) are usually sputter-deposited. Thin films are capable of faster response and recovery time. With the capacitive sensing material as described herein, the titanium dioxide and the platinum (particles) can be deposited by means of drop casting, inkjet printing or automated spotting. Spotting is preferred when the particles in the dispersion are too large for the inkjet nozzle.

The invention also provides a method for manufacturing a coated chip, preferably a capacitive chip as described herein, comprising:
i) applying a capacitive sensing material as described herein and/or a capacitive sensing coating formulation as described herein onto a chip, thereby forming a coated chip.

The method for manufacturing a chip may further comprise a step of drying the chip onto which a capacitive sensing material and/or a capacitive sensing coating formulation is applied. The optional drying step particularly removes at least part of any liquid present on the chip, such as solvent(s). The drying step may be performed at room temperature or at a temperature of at least 25° C., such as 30-150° C., 35-130° C., or 40-100° C. In particular, the drying step may be performed at 45-80° C., such as 50-70° C. Unlike with methods known from the art, this method advantageously does not require any heat treatment step(s), such as calcination and/or flame pyrolysis, to obtain a coated chip. Accordingly, a method is provided with which chips can be coated that comprise vulnerable (sensitive) electrodes without having to use high temperature coating conditions.

The invention further provides a method for sensing a gas in a gaseous mixture, comprising preferably at least hydrogen, the method comprising:
i) contacting the gaseous mixture with the capacitive sensing material of the invention, and ii) measuring a change in dielectric properties of the capacitive sensing material.

The method for sensing a gas in a gaseous mixture, as described herein, may further comprise one or more of the following steps:

iii) providing an energy input to a chip whereon the capacitive sensing material is present, for example a capacitive sensing chip, such as the capacitive sensing chip as described herein, that is converted to output signals based on at least one property, which at least one property is responsive to at least part of the gaseous mixture when exposed thereto, e.g. at step i), and iv) obtaining the output signals, wherein optionally the output signals are data signals. Sensing refers to determining any composition parameter of the gaseous mixture, including the relative concentrations of one or more of the gases present in the gaseous mixture.

In an embodiment, the gaseous mixture in the method for sensing a gas in a gaseous mixture as described above, comprises hydrogen.

In another embodiment, the method for sensing a gas in a gaseous mixture as described above is used to sense hydrogen (gas).

The method comprises contacting the gaseous mixture with at least parts of the sensing material, in particular exposing the porous titanium dioxide and platinum particles, preferably at least the platinum particles, of the capacitive sensing material with the gaseous mixture. Preferably, the method comprises continuously contacting a gaseous mixture with the capacitive sensing material, in particular constant exposure of the capacitive sensing material to the gaseous mixture. For example, the method may comprise passing the gaseous mixture over the capacitive sensing material. This is for example useful for methods for determining the composition, such as detecting the presence of hydrogen. The gaseous mixture does not need dilution nor is a carrier gas required. Typically, the gaseous mixture may be passed over the capacitive sensing material by convective flow, for example caused by the flow of the gaseous mixture in a space, such as a pipeline. The method may further optionally comprise a pre-treatment of the gaseous mixture prior to contact with the capacitive sensing material. For instance, the pre-treatment may involve removing at least some non-gaseous contaminations from the gaseous mixture, such as (liquid) droplets and (solid) particles. For instance, the method may comprise filtering to trap dust and droplets to prevent contamination of the capacitive sensing material. The method may also comprise contacting the capacitive sensing material to an atmosphere where hydrogen leakage is expected, thus measuring the presence of low concentrations of hydrogen caused by leaking pipes, valves, etc.

The capacitive sensor as described herein optionally measures in addition one or more properties of the gaseous mixture that are not related to its composition, such as pressure and temperature, and the flow rate in case of a gaseous stream, and optionally comprises sensor elements for these properties. Additional sensor elements can be added to measure other parameters of the gaseous mixture, such as thermal conductivity, viscosity, density, speed of sound or heat capacity. Preferably the thermal conductivity of the gaseous mixture is measured, since the thermal conductivity of hydrogen is much larger than other components in fuel gasses. This improves the reliability of the hydrogen content measurement, done by the capacitive sensing chip.

In an embodiment, the method for analysing the composition of a gaseous mixture, comprising at least hydrogen, as described herein is performed with a sensor comprising the capacitive sensing material as described herein, such as the capacitive sensor according to the invention. Optionally the method (further) involves determining one or more properties of the gaseous mixture, such as the amount of hydrogen (gas), with or without an intermediate step of calculating the concentration of one or more gases.

In an embodiment, a method is provided for analysing the composition of a gaseous mixture, comprising at least hydrogen, the method comprising:

i) contacting the gaseous mixture with a sensor, wherein the sensor comprises at least one sensor element, wherein the at least one sensor element comprises a coating, having at least one property that is responsive to at least part of the gaseous mixture when exposed thereto, wherein the sensor elements optionally differ at least in the composition of the coating, ii) providing an energy input to the sensor element that is converted to output signals based on the at least one property, and iii) obtaining the output signals, wherein optionally the output signals are data signals, wherein the sensor is the capacitive sensor as described herein, wherein the sensor element is optionally the capacitive chip as described herein, and wherein the coating of the sensor element is optionally the capacitive sensing material as described herein. The method comprises contacting the gaseous mixture with at least parts of the sensor, in particular exposing the coating of the sensor elements to the gaseous mixture. Preferably, the method comprises continuously contacting a gaseous mixture with the sensor, in particular constant exposure of the capacitive sensing material to the gaseous mixture. For example, the method may comprise passing the gaseous mixture over the sensor elements. This is for example useful for methods for determining the composition. The gaseous mixture does not need dilution nor is a carrier gas required. Typically, the gaseous mixture may be passed over the sensor elements by convective flow, for example caused by the flow of the gaseous mixture in a space, such as a pipeline. The method may further optionally comprise a pre-treatment of the gaseous mixture prior to contact with the sensor. For instance, the pre-treatment may involve removing at least some non-gaseous contaminations from the gaseous mixture, such as (liquid) droplets and (solid) particles. For instance, the method may comprise filtering to trap dust and droplets to prevent contamination of the sensor.

The method may comprise a transducer, which is generally configured for converting an energy input to an output signal, preferably a data signal. Suitable energy input as described herein include for example an electric current, an electromagnetic wave, an optical signal, a vibration, a chemical reaction, a physical process. The output signal is typically an electronic signal. The method may therefore comprise a step of providing an energy input to the transducer(s). The energy input is converted into output signals. An embodiment of the method may involve providing an electric current to a transducer, such that data signals are obtained from the transducer as an electric signal, such as an analogous or digital signal.

The method as described herein may further comprise one or both of the following steps:

iv) providing the output signals and/or data signals to a computer processor which is in communication with a computer memory device in which instructions are stored for conversion of the data signals to an estimated composition parameter, and v) calculating in the computer processor the estimated composition parameter using the instructions and the output signals and/or data signals.

Optionally, the sensor (used in the methods) as described herein comprises a data acquisition system as is conventional, for example comprising signal conditioning circuitry to convert sensor (output) signals into a form that can be converted to digital values, and analogue-to-digital converters, which convert conditioned sensor signals to digital values. Such digital output signal can be used for calculations.

Suitable computer memory devices include computer memory, for example $E^2$PROM (Electrically Erasable Programmable Read-Only Memory), flash, and a hard disk. Suitable processors include all types of microprocessors, such as a microcontroller and a central processing unit.

The computer processor may be in communication with the capacitive chip via, e.g. analogue/digital conversion chips such as an AD7745 or AD7746 capacitance to Digital converter and typically stores values of the output signal in a computer memory. For example, the stored values are read by the processor with some frequency. For instance, the values can be used to calculate the hydrogen concentration and/or one or more other properties of the gaseous mixture, for instance according to a schedule or at certain intervals. The processor is accordingly typically adapted, programmed and/or configured for calculating the hydrogen concentration and/or one or more other composition parameters of the gaseous mixture using the output signals from the capacitive chip. Preferably, each sensor element is connected to a sensor interface circuit, which transports the signals from the sensor elements, or sensor, to a processor. The processor which calculates the composition parameters can be connected to the sensor elements, or sensor, for example wired, wireless or through a network such as the internet.

The methods as described herein may be methods of inline analysis of the composition of the gaseous stream, preferably for determining the hydrogen concentration. The sensor is accordingly preferably an inline device mountable or mounted to, or integrated in a pipeline segment or flow meter. In that case preferably the step of contacting the gaseous mixture with the sensor comprises flowing at least part of the gaseous mixture over the sensor elements.

The gaseous mixture may comprise minor amounts of a liquid (typically less than 5% by total volume of the mixture, preferably less than 1% by total volume of the mixture) or solid material (typically less than 1% by total volume of the mixture, preferably less than 0.1%), for example dust. The gaseous mixture may be the atmosphere as described above or is transported by flowing through a pipeline or tube. The method may also comprise the measurement of properties of a non-flowing gaseous mixture (such as the atmosphere as described herein), for example of a sample, such as an air sample.

The gaseous mixture may be a gaseous stream of, for example, natural gas, syngas, biogas, expanded liquefied natural gas or a mixture comprising two or more thereof. In case of natural gas, the gaseous stream typically comprises at least 70% by total volume of the gaseous stream of methane, 1-10% by total volume of the gaseous stream of total $C_2$-$C_6$ alkanes, in particular ethane and propane, 0.2-20% by total volume of the gaseous stream of nitrogen, and 0.5-5% by total volume of the gaseous stream of carbon dioxide. Raw biogas is different to natural gas, and typically comprises 50-75% by total volume of methane, 25-50% by total volume of carbon dioxide, 0-10% by total volume of nitrogen, 0-1% by total volume of hydrogen, 0-3% by total volume of hydrogen sulphide and 0-1.0% by total volume of other components. Cleaned biogas typically comprises 95-55% by total volume of methane, 0.5-20% by total volume of carbon dioxide, and 0-20% by total volume of nitrogen. Preferably, the sensing material of the invention is suitable for both natural gas and biogas.

The methods as described herein may be carried out at a temperature between −20° C. and 100° C., such as room temperature, i.e. the gaseous mixture to which the capacitive sensing material is exposed has a temperature in such range.

The term "room temperature" as used herein is defined as the average indoor temperature to the geographical region where the invention is applied. Typically, the room temperature is 20° C.

The methods preferably do not alter the composition of the gaseous mixture, for example as a consequence of chemical reactions resulting in the formation and release of chemical compounds that were not in the gaseous mixture prior to performing the method.

In particular, regarding the method for analysing the composition of a gaseous mixture as described herein, the estimated composition parameter is hydrogen and/or the hydrogen concentration.

The method for analysing the composition of a gaseous mixture may be performed in an oxygen-free atmosphere.

The invention also provides a use of particles comprising titanium oxide and platinum for sensing hydrogen (gas), i.e., their use as hydrogen (gas) sensing material. Titanium oxide preferably refers to titanium dioxide. In particular, the particles comprising titanium dioxide and platinum are composite particles comprising porous titanium dioxide and platinum, such as porous core-shell nanoparticles. Preferably, the core of the porous core-shell particles comprises titanium dioxide, whereas the porous shell comprises platinum nanoparticles. As mentioned herein, the inventors surprisingly found that such material is highly sensitive to detecting hydrogen (gas).

In an embodiment, a gas sensor is provided comprising the capacitive sensing material as described herein, which can be used for detecting gas(es), such as hydrogen, for example of leaks from pipelines for gas streams, in particular of hydrogen leakage, for example in gas production. Such a sensor, or gas leak detector, can for example be placed on the inside and/or outside of a pipeline. Accordingly, the invention also relates to the use of a capacitive sensing material as described herein for detecting a gas leak, e.g. in a pipeline. All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variation of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject-matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the invention may include embodiments having combinations of all or some of the features described. The invention will now be further illustrated by the following non-limiting examples.

EXAMPLES

Example 1—Synthesis of Porous Titanium Dioxide Particles 8 ml 0.1 M KCl was added to 1580 g ethanol and the solution was stirred for 10 min in a 2 l reactor. After 10 min 30.6 ml of titanium isopropoxide was added at a stirring speed of 300 rpm, after addition the stirring speed was set to 200 rpm. The dispersion was stirred overnight.

After overnight stirring a white dispersion was obtained which was centrifuged at 6000 rpm. After removal of the supernatant to the obtained sedimented material was added ethanol again a centrifuge step was used, this was repeated twice with water and after the last centrifuge step the sedimented material was dispersed in 200 ml demineralised water. The obtained dispersion was given an ultrasonic treatment in an ultrasonic bath. The average particle size was 300 nm (FIG. 1).

Example 2—Growing of Platinum Nanoparticles in the Porous Titanium Dioxide Particles A 2 l reactor was heated to 60° C. 1000 ml demineralised water was added to the reactor. 0.36 g chloroplatinic acid was added to 500 ml demineralised water. 4.53 g polyvinylpyrrolidone (PVP) was added while stirring/shaking. The mixture was stirred until all PVP is dissolved. This was added to 1000 ml demineralised water which was in the 2 l reactor. After 5 min of stirring, 150 ml of the 0.1 wt. % titanium dioxide dispersion was added under stirring. The mixture was heated until the temperature of the dispersion was 50° C. At 50° C., a solution of 1.8 g $NaHB_4$ in 150 ml demineralised water was slowly added using a droplet addition system. The mixture was stirred for 2 hours at 50° C. and then centrifuged at 6000 rpm for 30 min. Then, the material was washed two times with 1 l demineralised water. After the final centrifuge step in 200 ml total was dispersed.

Figure 2:
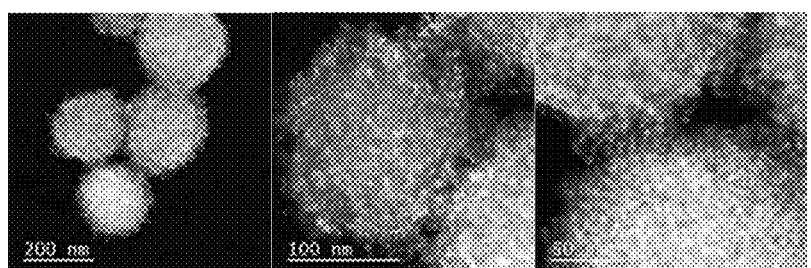
FIG. 2 displays TEM images of the titanium dioxide particles comprising impregnated platinum nanoparticles.

The concentration of platinum in the particles was 25 wt. % according to inductively coupled plasma (ICP) measurements. FIG. 2 displays TEM images of the titanium dioxide particles comprising impregnated platinum nanoparticles.

Figure 3:
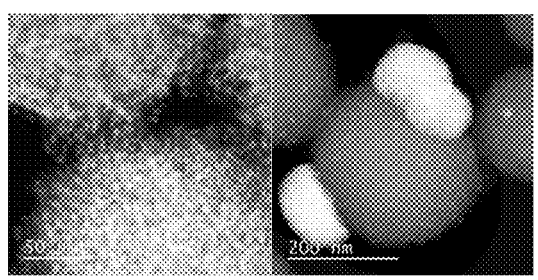
FIG. 3 displays TEM images of titanium dioxide particles having surface-grown palladium particles.

Example 3—Growing of Palladium Particles on the Porous Titanium Dioxide Particles 0.1 g tetrachloropalladate ($PdCl_4$) was added to 12 ml (50 mM) HCl. After 5 min, 540 ml demineralised water was added. After 10 min, 180 ml of 0.1 wt. % titanium dioxide dispersion was added to this 1 mM $H_2PdCl_4$ solution, under stirring. Then, 50 ml of 100 mM ascorbic acid solution was added under stirring. The dispersion was stirred for 60 min. After this the dispersion was given a centrifuge step, 6000 rpm for 20 min, to obtain the $TiO_2$/Pd particles, the material was washed three times with demineralised water and centrifuged. The $TiO_2$/Pd material was dispersed in 80 ml demineralised water. The amount of palladium on the particles was ca. 5 wt. % using ICP measurements. FIG. 3 displays TEM images of titanium dioxide particles having surface grown palladium particles.

Example 4—Hydrogen Sensing with $TiO_2$/Pt Coating

Figure 4:
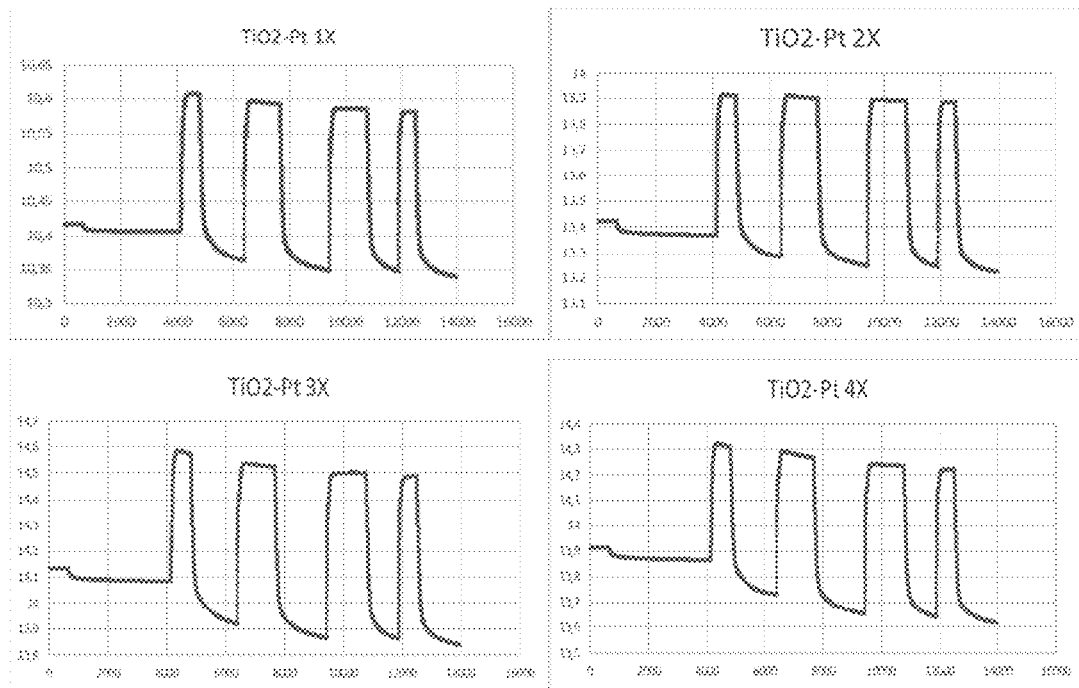
FIG. 4 displays hydrogen sensing with $TiO_2$/Pt coating wherein the response to hydrogen increased between 1 and 2 times coating, but stayed constant for 2 to 4 times coating (FIG. 4).

The $TiO_2$/Pt particles from example 2, were applied to a chip having interdigitated electrodes. The capacitance of the empty chip was 7 pF. The coating process was done one time, two times, three times and four times in order to assess the influence of the coating thickness on the response. This increased the capacitance of the chip to 10.4 pF, 13.4 pF, 14.1 pF and 13.9 pF, respectively. When this coated chip is exposed to 5 vol. % hydrogen in nitrogen, a significant response was measured. Even for the thickest coating, there was no short circuit of the capacitive electrodes. This was one of the risks identified, because the $TiO_2$/Pt may give a conductive layer. The response to hydrogen increased between 1 and 2 times coating, but stayed constant for 2 to 4 times coating (FIG. 4).

Example 5—Comparison Between $TiO_2$/Pt Coating and Thermal Conductivity Sensor (TCD)

Figure 5:
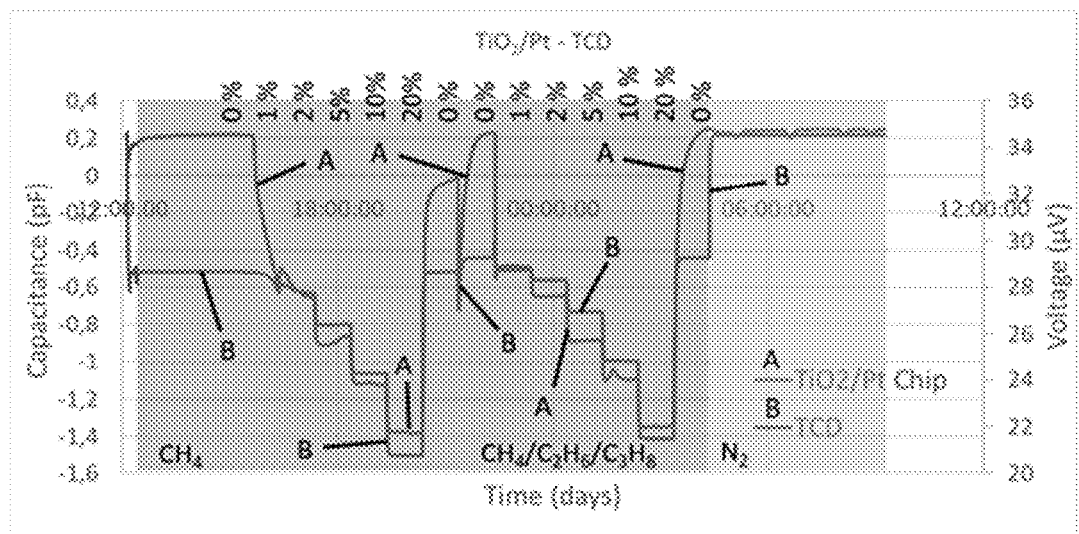
FIG. 5 displays a comparison between $TiO_2$/Pt coating and thermal conductivity sensor (TCD) where the experiment was performed with hydrogen mixtures in methane and methane/ethane/propane/nitrogen at 0, 1, 2, 5, 10 and 20 vol. % at 1 bara.

The new sensor, including the TCD and the chips coated with the titanium dioxide coating were inserted in the pressure vessel of the Gas Exposure System. Three sets of experiments were done:
  hydrogen mixtures in methane and methane/ethane/propane/nitrogen at 0, 1, 2, 5, 10 and 20 vol. % at 1 bara (FIG. 5);
  hydrogen mixtures in methane and methane/ethane/propane/nitrogen at 0, 1, 2, 5, 10 and 20 vol. % at 3 bara, and
  hydrogen mixtures in nitrogen at 0, 125, 250, 375 and 500 ppm at 1 bara.

The response of the coated chip to small changes in hydrogen concentrations was very high. Responses of 1.5 pF are very significant and open the possibilities of measuring hydrogen concentration at ppm levels. This was done using a gas mixture of 0.05 vol. % hydrogen in nitrogen. It was observed that the TCD registers a difference in signal when changing from methane to nitrogen, but the coated chip hardly measures a difference between nitrogen and hydrocarbons.

Figure 6:
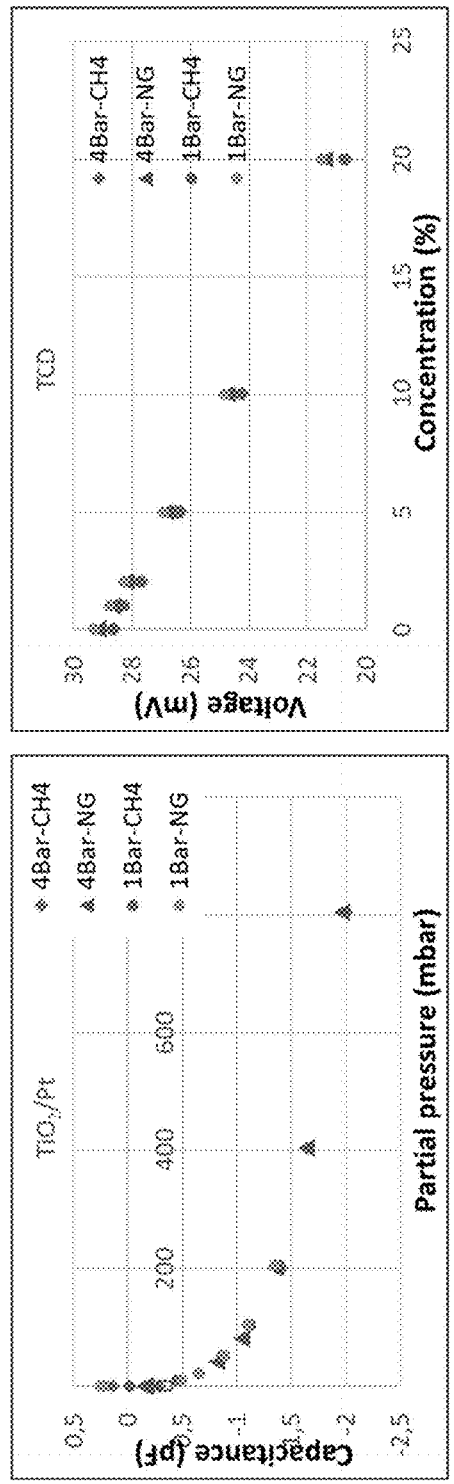
FIG. 6 displays a comparison between $TiO_2$/Pt coating and thermal conductivity sensor (TCD). The coated chip is only sensitive for hydrogen partial pressure, but the TCD is sensitive for the total gas composition and hydrogen concentration.

Both sensors ($TiO_2$/Pt and TCD) are only slightly dependent on the flow rate of the gas. Furthermore, both sensors are also sensitive to changes in pressure. However, when no hydrogen is present, the coated chip shows no response, but the TCD does. Apparently, the coated chip is only sensitive for hydrogen partial pressure, but the TCD is sensitive for the total gas composition and hydrogen concentration. This is shown in more detail in FIG. 6.

Figure 7:
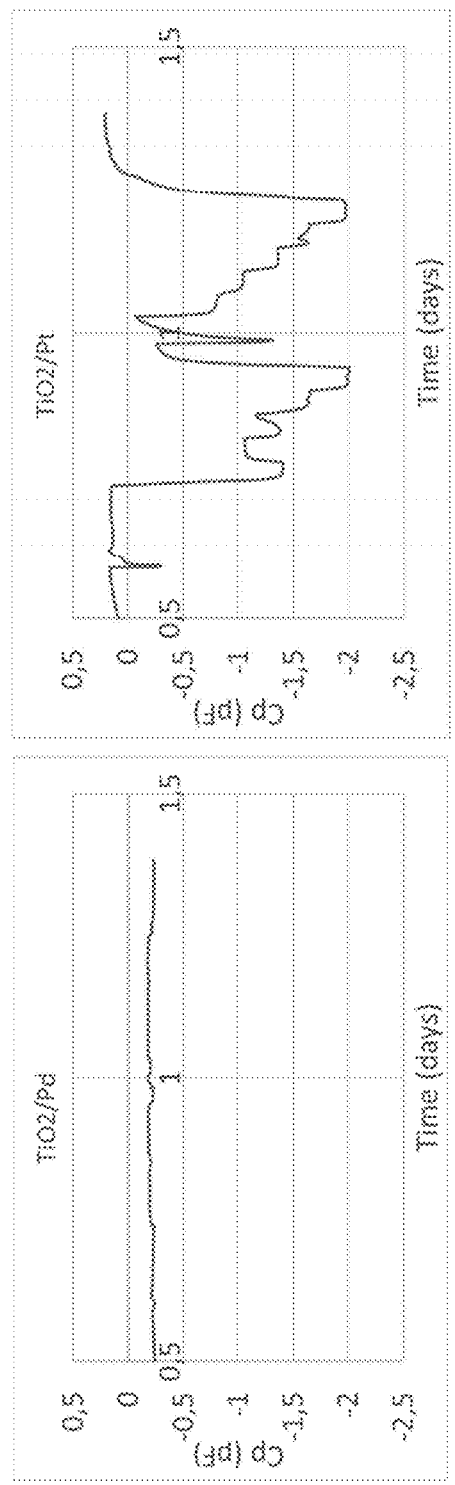
FIG. 7 shows that the platinum chip shows a very high response, whereas the palladium chip does not respond at all.

Example 6—Comparison Between Platinum and Palladium Coated Titanium Dioxide Particles Two capacitive sensor chips were prepared by coating the capacitive sensing material on the interdigitated electrodes. The two chips were exposed to the same variations in hydrogen concentration in methane and natural gas. FIG. 7 shows that the platinum chip shows a very high response, whereas the palladium chip does not respond at all.

The invention claimed is:

1. A capacitive sensing material, which is used at room temperature, comprising composite particles having an average particle size of 50-500 nm, as measured with transmission electron microscopy; wherein the composite particles comprise porous titanium dioxide having pores is at least in part coated with platinum particles, the porous titanium dioxide is 10-80% by total weight of the composite particles, the platinum particles are impregnated in at least part of the pores of the porous titanium dioxide, and the platinum particles have an average particle size of 1-20 nm.

2. The capacitive sensing material of claim 1, wherein the amount of platinum is 10-45% by total weight of the composite particles.

3. The capacitive sensing material of claim 1, having selectivity for adsorption and/or absorption of hydrogen.

4. A capacitive sensing coating formulation, comprising the capacitive sensing material of claim 1.

5. A capacitive chip, comprising the capacitive sensing material of claim 1 or a capacitive sensing coating formulation comprising the capacitive sensing material.

6. A method for manufacturing a capacitive chip of claim 5, comprising:
i) applying the capacitive sensing material and/or a capacitive sensing coating formulation which comprises the capacitive sensing material, onto a chip, thereby forming a coated chip.

7. A method for manufacturing the capacitive sensing material of claim 1, the method comprising:
i) preparing a dispersion comprising porous titanium dioxide particles, and
ii) coating the porous titanium dioxide particles with platinum particles, thereby forming the capacitive sensing material.

8. The method of claim 7, wherein step ii) is performed at a temperature of 20-150° C.

9. A method for sensing a gas in a gaseous mixture, the method comprising:
i) contacting the gaseous mixture with the capacitive sensing material as described in claim 1, and
ii) measuring a change in capacitance of the capacitive sensing material.

10. The method of claim 9, further comprising:
iii) providing an energy input to a chip, whereon the capacitive sensing material is present, that is converted to output signals based on at least one property, which at least one property is responsive to at least part of the gaseous mixture when exposed thereto.

11. The method of claim 9, wherein the gaseous mixture is a gaseous stream of natural gas, syngas, biogas, expanded liquefied natural gas, or a mixture thereof.

12. The method of claim 9, wherein the gaseous mixture comprises at least hydrogen.

13. The method of claim 9, further comprising:
iv) providing output signals and/or data signals to a computer processor which is in communication with a computer memory device in which instructions are stored for conversion of the data signals to an estimated composition parameter, and
v) calculating in the computer processor the estimated composition parameter using the instructions and the output signals and/or data signals, and wherein the estimated composition parameter is preferably the hydrogen concentration.

14. The method of claim 9, wherein the method is performed in an oxygen-free atmosphere.

15. The method of claim 9, wherein the method is performed at room temperature.

16. A capacitive sensor, comprising:
(A) a capacitive sensing material that is usable at room temperature; wherein the capacitive sensing material comprises composite particles having an average particle size of 50-500 nm, as measured with transmission electron microscopy, wherein the composite particles comprise porous titanium dioxide having pores is at least in part coated with platinum particles, the porous titanium dioxide is 10-80% by total weight of the composite particles, the platinum particles are impregnated in at least part of the pores of the porous titanium dioxide, and the platinum particles have an average particle size of 1-20 nm; and
(B) a capacitive chip; wherein the capacitive chip comprises the capacitive sensing material.

17. The capacitive sensor of claim 16, being a capacitive gas sensor.

18. The capacitive sensor of claim 16, further comprising one or more additional (capacitive) chips comprising one or more coatings.

19. The capacitive sensor of claim 16, further comprising one or more additional sensing elements for measuring physical gas properties.

20. The capacitive sensor of claim 19, wherein the physical gas properties are selected from the group consisting of pressure, temperature, thermal conductivity, viscosity, speed of sound, density, and heat capacity.

21. The capacitive sensor of claim 19, comprising a thermal conductivity sensing element.

22. The capacitive sensor of claim 16, suitable for measurement of hydrogen concentrations between 0.01-100 vol. % by total gas volume measured.

* * * * *